United States Patent
Gao et al.

(10) Patent No.: US 9,683,948 B2
(45) Date of Patent: Jun. 20, 2017

(54) SYSTEMS AND METHODS FOR ITERATIVE MULTI-MATERIAL CORRECTION OF IMAGE DATA

(71) Applicant: General Electric Company, Schenectady, NY (US)

(72) Inventors: Hewei Gao, Waukesha, WI (US); Girijesh K. Yadava, Waukesha, WI (US); Adam Israel Cohen, Milwaukee, WI (US); Brian Edward Nett, Wauwatosa, WI (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 26 days.

(21) Appl. No.: 14/070,252

(22) Filed: Nov. 1, 2013

(65) Prior Publication Data

US 2015/0125055 A1 May 7, 2015

(51) Int. Cl.
*G06K 9/00* (2006.01)
*G01N 23/04* (2006.01)
*A61B 6/00* (2006.01)
*A61B 6/03* (2006.01)
*G06T 11/00* (2006.01)
*A61B 8/08* (2006.01)

(52) U.S. Cl.
CPC .......... *G01N 23/046* (2013.01); *A61B 6/032* (2013.01); *A61B 6/5211* (2013.01); *A61B 6/5258* (2013.01); *A61B 6/583* (2013.01); *G06T 11/005* (2013.01); *A61B 6/482* (2013.01); *A61B 8/0875* (2013.01); *G01N 2223/42* (2013.01)

(58) Field of Classification Search
None
See application file for complete search history.

(56) References Cited

U.S. PATENT DOCUMENTS

| | | |
|---|---|---|
| 5,953,444 A | 9/1999 | Joseph |
| 7,298,812 B2 | 11/2007 | Tkaczyk et al. |
| 7,315,604 B2 | 1/2008 | Raupach |
| 7,391,844 B2 | 6/2008 | Wu et al. |
| 7,444,010 B2 | 10/2008 | DeMan |
| 7,747,057 B2 | 6/2010 | Wu et al. |
| 7,801,264 B2 | 9/2010 | Wu et al. |
| 7,822,172 B2 | 10/2010 | Ruhrnschopf et al. |
| 7,949,088 B2 | 5/2011 | Nishide |

(Continued)

OTHER PUBLICATIONS

U.S. Appl. No. 13/677,010, filed Nov. 14, 2012, Xiaoye Wu et al.

(Continued)

*Primary Examiner* — Weiwen Yang
(74) *Attorney, Agent, or Firm* — Fletcher Yoder, P.C.

(57) ABSTRACT

Systems and methods for iterative multi-material correction are provided. A system includes an imager that acquires projection data of an object. A reconstructor reconstructs the acquired projection data into a reconstructed image, utilizes the reconstructed image to perform a multi-material correction on the acquired projection data to generate a multi-material corrected reconstructed image, and utilizes the multi-material corrected reconstructed image to perform one or more iterations of the multi-material correction on the projection data to generate an iteratively corrected multi-material corrected image.

19 Claims, 7 Drawing Sheets

(56) References Cited

U.S. PATENT DOCUMENTS

| | | | |
|---|---|---|---|
| 2006/0159223 A1* | 7/2006 | Wu | A61B 6/032 378/18 |
| 2011/0044559 A1 | 2/2011 | Erhard et al. | |
| 2011/0097007 A1* | 4/2011 | Zeng et al. | 382/260 |
| 2011/0103542 A1* | 5/2011 | Allmendinger et al. | 378/4 |
| 2012/0263360 A1* | 10/2012 | Zhu et al. | 382/131 |
| 2014/0056407 A1* | 2/2014 | Goldammer et al. | 378/62 |

OTHER PUBLICATIONS

Kasperl, Stefan, et al.; "Computed Tomography Metrology in Industrial Research & Development", International Symposium on NDT in Aerospace, Dec. 2008, pp. 1-7.

Stenner, Philip, et al.; "Dynamic Iterative Beam Hardening Correction (DIBHC) for an Optimized Assessment of Cardiac Perfusion in ECG-Correlated CT", 2009 IEEE Nuclear Science SYMPOSIUM Conference Record, pp. 3523-3530.

Dembowski; "IAR—Artifact Reductions in Computed Tomography", Fraunhofer Institute for Integrated Circuits, Development Center X-Ray Technology, 2010, pp. 1-6.

Krumm, Michael, et al.; "Beam Hardening Correction of Multi-Material Objects", Fraunhofer Development Center X-Ray Technology, 2010, pp. 1-7.

van Gompel, G., et al.; "Iterative Correction of Beam Hardening Artifacts in CT", Med. Phys. vol. 38, No. 7, pp. S36-S49.

Yang, G., et al.; "Accelerated Quantitative Multi-Material Beam Hardening Correction (BHC) in Cone-Beam CT", European Society of Radiology 2012, pp. 1-13.

\* cited by examiner

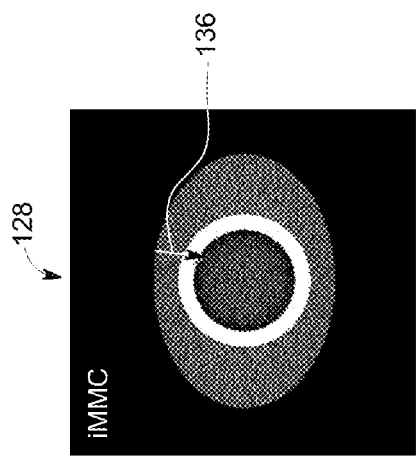
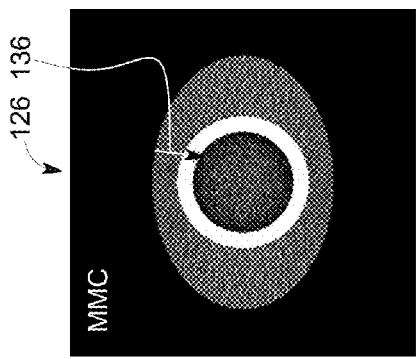
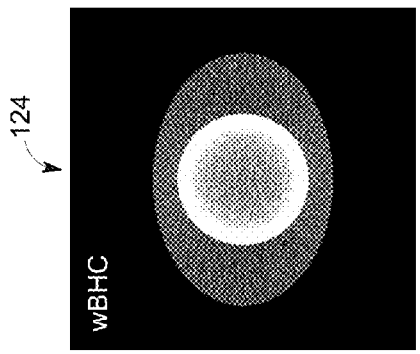
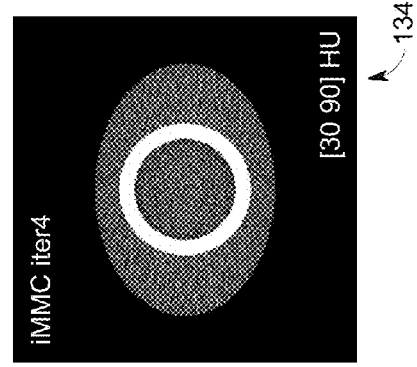
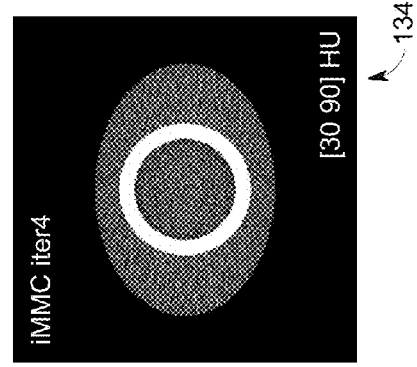
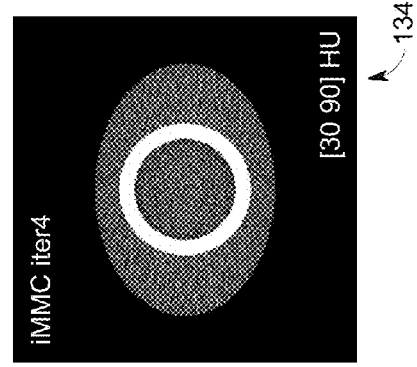

SYSTEMS AND METHODS FOR ITERATIVE MULTI-MATERIAL CORRECTION OF IMAGE DATA

BACKGROUND

The subject matter disclosed herein relates generally to imaging techniques and, more particularly, to systems and methods for performing iterative multi-material correction of image data.

Non-invasive imaging technologies enable images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation spans a subject of interest, such as a human patient, and a portion of the radiation impacts a detector where the image data is collected. In digital X-ray systems, a photodetector produces signals representative of the amount or intensity of radiation impacting discrete pixel regions of a detector surface. The signals may then be processed to generate an image that may be displayed for review. In CT systems, a detector array, including a series of detector elements, produces similar signals through various positions as a gantry is displaced around a patient.

In the images produced by such systems, it may be possible to identify and examine the internal structures and organs within a patient's body. However, the produced images may also include artifacts that adversely affect the quality of the images due to a variety of factors. For example, these factors may include beam hardening for non-water materials, heel-effect related spectral variation in wide cone CT systems, bone induced spectral (BIS) due to detection variation of different detector pixels coupled to spectral changes attenuated by bone or other non-water materials, and other factors. Accordingly, a variety of techniques have been developed to attempt to correct for these artifacts.

For example, multi material correction (MMC) is an algorithm developed for spectral calibration (i.e., beam hardening correction (BHC)) for wide-cone CT. However, a key assumption in MMC is that the re-projection of iodine in the first-pass CT images approximates the polychromatic projection of iodine after water BHC. MMC is therefore typically limited to a one-step correction procedure, thus limiting the extent to which beam hardening effects can be corrected and requiring post-processing parameter tuning. Accordingly, there exists a need for systems and methods that address these drawbacks.

BRIEF DESCRIPTION

In one embodiment, a method includes acquiring projection data of an object from a plurality of pixels, reconstructing the acquired projection data from the plurality of pixels into a reconstructed image, and performing material characterization and decomposition of an image volume of the reconstructed image to reduce a number of materials analyzed in the image volume to two basis materials. One of the two basis materials is the material that has been used in the single-material beam hardening correction (e.g., water from water BHC). The method also includes generating a re-mapped image volume for that said material, performing forward projection on at least the re-mapped image volume for that said material to produce a material-based projection, generating multi-material corrected projections based on the material-based projection and a total projection attenuated by the scanned object, reconstructing a multi-material corrected image from the multi-material corrected projections, and performing one or more iterations of a multi-material correction on the multi-material corrected image.

In another embodiment, a method includes acquiring first projection data of an object from a plurality of pixels. The first projection data includes a first acquired view of the object. The method also includes reconstructing the acquired first projection data from the plurality of pixels into a reconstructed image, performing material characterization and decomposition of an image volume of the reconstructed image to reduce a number of materials analyzed in the image volume to two basis materials and performing forward projection for the first acquired view of the object, performing a multi-material correction for the first acquired view of the object to generate a first multi-material corrected projection, updating the reconstructed image based on the first multi-material corrected projection to generate an updated reconstructed image, and acquiring additional projection data of an object from a plurality of pixels. The additional projection data includes a plurality of acquired views of the object acquired one at a time. The method further includes performing, one at a time for each of the plurality of acquired views of the object, material characterization and decomposition of an image volume of the updated reconstructed image and forward projection, performing a multi-material correction for each of the plurality of acquired views of the object one at a time to generate a plurality of multi-material corrected projections, and updating the updated reconstructed image based on the plurality of multi-material corrected projections as the plurality of multi-material corrected projections are generated.

In another embodiment, a system includes an imager that acquires projection data of an object. The projection data includes a plurality of projection views. A processor generates a multi-material corrected, reconstructed image of the object, generates a plurality of multi-material corrected projection views by materially decomposing, forward projecting, and multi-materially correcting each of the plurality of projection views, and updates the multi-material corrected, reconstructed image of the object with each of the plurality of multi-material corrected projection views.

In another embodiment, a system includes an imager that acquires projection data of an object. A reconstructor reconstructs the acquired projection data into a reconstructed image, utilizes the reconstructed image to perform a multi-material correction on the acquired projection data to generate a multi-material corrected reconstructed image, and utilizes the multi-material corrected reconstructed image to perform one or more iterations of the multi-material correction on the projection data to generate an iteratively corrected multi-material corrected image.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 4A illustrates an example of an image of an elliptical water phantom reconstructed using water beam hardening correction;

FIG. 4B illustrates an example of an image of an elliptical water phantom reconstructed using multi-material correction;

FIG. 4C illustrates an example of an image of an elliptical water phantom reconstructed using one round of iterative multi-material correction;

FIG. 4D illustrates an example of an image of an elliptical water phantom reconstructed using two rounds of iterative multi-material correction;

FIG. 4E illustrates an example of an image of an elliptical water phantom reconstructed using three rounds of iterative multi-material correction;

FIG. 4F illustrates an example of an image of an elliptical water phantom reconstructed using four rounds of iterative multi-material correction;

DETAILED DESCRIPTION

Figure 1:
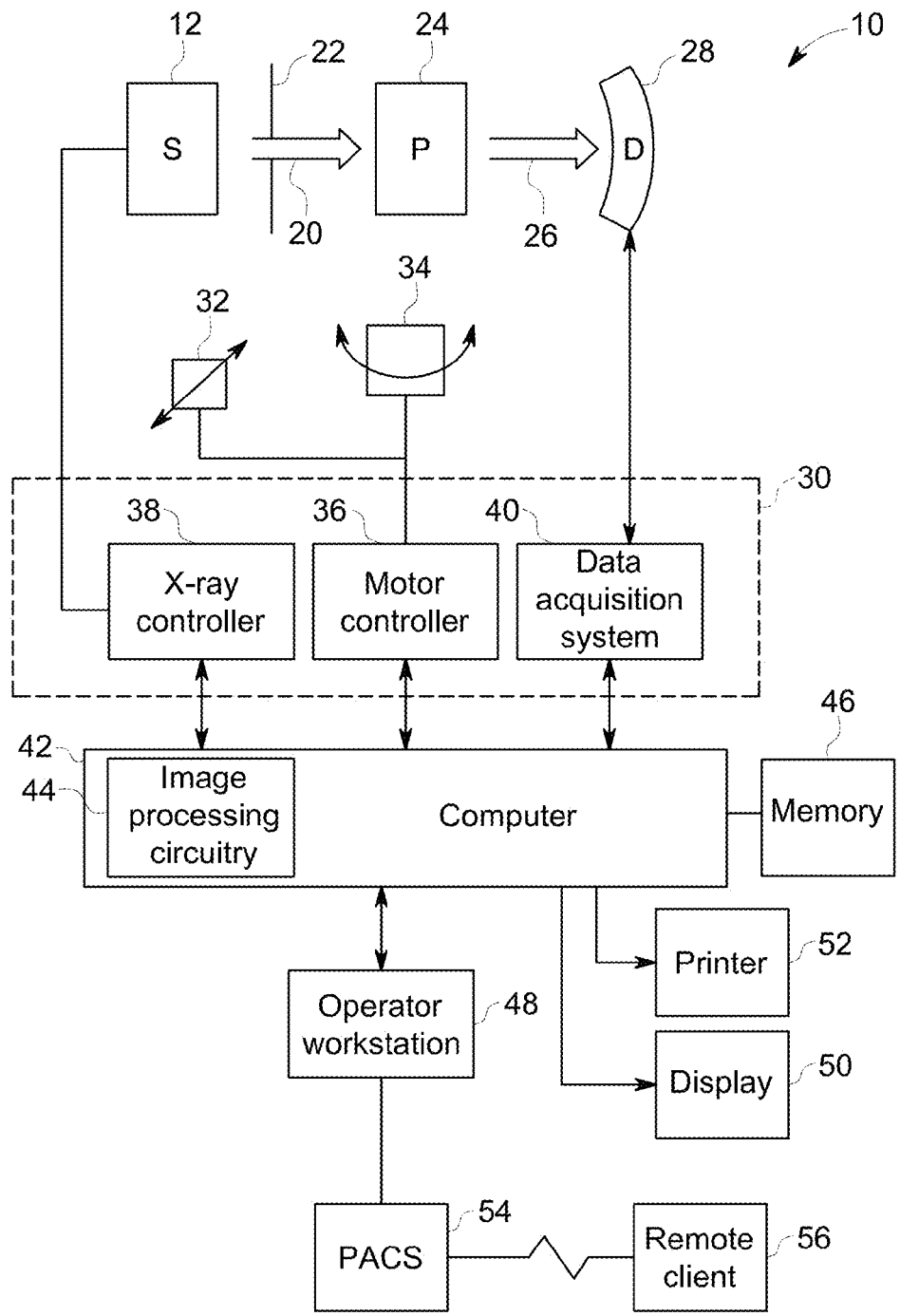
FIG. 1 is a schematic illustration of an embodiment of a computed tomography (CT) system capable of acquiring CT images of a patient processing the images in accordance with aspects of the present disclosure.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

Tissue characterization or classification may be desirable in various clinical contexts to assess the tissue being characterized for pathological conditions and/or to assess the tissue for the presence of various elements, chemicals or molecules of interest. However, tissue characterization in imaging studies, such as using computed tomography (CT), may be problematic due to the presence of artifacts present within the reconstructed images. These artifacts may be present due to a variety of sources. For instance, due to the nature of a polychromatic X-ray beam produced by the Bremsstrahlung process, the beam attenuated by different materials of an imaged subject will result in different exit beam spectra. The effect of the polychromatic nature of the input X-ray spectra and the energy-dependent nature of material attenuation by different materials induces "beam hardening" artifacts in the reconstructed image. In addition, the mean value of a given material is not constant. For example, presently the CT value of a non-water material is a function of the incident beam, location of the materials, type of reconstruction due to weighting, and adjacent materials around a region of interest (ROI). However, from a physics point of view, the presence of the beam hardening artifact is due to the fact that the measured projection of a given type of material is not linearly proportional to the length of the material at different view angles.

Further factors also result in artifacts in the reconstructed images. For example, the "heel-effect" causes incident beam spectrum variation inside a wide cone angle, especially a beam with a few degrees take-off angle from the anode. The heel-effect results in different mean values of non-water materials across the cone angle. Other artifact-inducing factors arise due to imperfections present in clinical CT detection systems. For example, each detector pixel might have a slightly different response to given incident spectrum, resulting in differential errors in detection when the incident beam is not purely water-attenuated, causing a bone-induced spectral (BIS) artifact. Typically, iterative bone option (IBO) and BIS correction techniques used to correct these artifacts are empirically based and/or are subject to error.

As discussed herein, in various implementations, an iterative multi-material correction (iMMC) approach is employed to compensate for the foregoing artifacts within the reconstructed images without under or over correction and without the use of tuning parameters. Traditional multi material correction (MMC) is an algorithm developed for spectral calibration (namely beam hardening correction, BHC) for wide-cone CT, and is described in detail in U.S. patent application Ser. No. 13/677,010, filed on Nov. 14, 2012, and entitled, "System and Method for Multi-Material Correction of Image Data," which is hereby incorporated by reference in its entirety for all purposes. Compared with the conventional BHC algorithms, an advantage of the MMC algorithm is that it avoids multi re-projections and high dimension (>2D) polynomial functions by converting the beam hardening of multi materials into just two basis materials (e.g., water and iodine). However, it is now recognized that some steps in the implementation of MMC are just approximations and residual errors could still exist in the second-pass correction term, $\Delta p$.

Some examples of errors that could be introduced are: initial reconstruction could suffer in incomplete data problem; image-based material decomposition could be affected by the remaining artifacts on the initial reconstructed image; re-projection of the equivalent iodine image is not exactly the iodine's projection pre-filtered by water due to the remaining beam hardening artifacts; re-projection could have difficulties when X or Z truncations occur. However, it should be noted that the main residual errors in MMC occur in the material decomposition step and the re-projection step.

It is now recognized that since the material decomposition errors and the re-projection errors are mainly due to the residual beam hardening artifacts in the first-pass reconstruction that are supposed to be further corrected by MMC, multiple rounds of MMC therefore may be helpful, and even necessary in some cases, in reaching the desired images for clinical use. However, known MMC implementations do not enable iteration because after MMC, re-projection of iodine becomes almost monochromatic, no longer approximating the polychromatic projection of iodine. Accordingly, the iMMC disclosed herein has been developed to support multiple, iterative rounds of MMC correction. As described in more detail below, in iMMC, re-projection of water instead of iodine is computed and used to estimate the second pass correction term in embodiments in which water and iodine are the two basis materials selected and water beam hardening correction (BHC) has been applied before the first-pass reconstruction, thus enabling iteration since re-projection of water is always treated as monochromatic. However, it should be noted that although water is used as an example in certain embodiments described herein, the material used in the estimation of the second pass correction term may vary in other embodiments. Indeed, in iMMC, re-projection of a single material of the two chosen basis materials that has been used in the single material BHC before the first pass reconstruction may be computed and used to estimate the second pass correction term. This single material is not limited to water, for example, in embodiments in which nondestructive testing is performed and the chosen basis materials are not iodine and water.

With the foregoing discussion in mind, FIG. 1 illustrates an embodiment of an imaging system 10 for acquiring and processing image data in accordance with aspects of the present disclosure. In the illustrated embodiment, system 10 is a computed tomography (CT) system designed to acquire X-ray projection data, to reconstruct the projection data into a tomographic image, and to process the image data for display and analysis. The CT imaging system 10 includes an X-ray source 12. The source 12 may include one or more X-ray sources, such as an X-ray tube or solid state emission structures. The X-ray source 12, in accordance with present embodiments, is configured to emit an X-ray beam 20 at one or more energies.

Although the following techniques discussed below utilize the emission of the beam at a single emission spectrum, the same techniques may be applied for the emission of the beam at two or more energies, although single-energy embodiments are discussed herein to simplify explanation. For example, the X-ray source 12 may be configured to switch between relatively low energy polychromatic emission spectra (e.g., at about 80 kVp) and relatively high energy polychromatic emission spectra (e.g., at about 140 kVp). Also, the X-ray source 12 may emit at polychromatic spectra localized around energy levels (i.e., kVp ranges) other than those listed herein (e.g., 100 kVP, 120 kVP, etc.). Indeed, selection of the respective energy levels for emission may be based, at least in part, on the anatomy being imaged.

In certain implementations, the source 12 may be positioned proximate to a collimator 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements. Each detector element produces an electrical signal that represents the intensity of the X-ray beam incident at the position of the detector element when the beam strikes the detector 28. Electrical signals are acquired and processed to generate one or more scan datasets.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28 in accordance with the steps and processes discussed herein. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. In addition, in some embodiments the X-ray controller 38 may be configured to selectively activate the source 12 such that tubes or emitters at different locations within the system 10 may be operated in synchrony with one another or independent of one another. The X-ray controller 38 is configured to control the source 12 to emit X-rays at a single polychromatic energy spectrum in an image acquisition sequence to acquire a single energy dataset. In certain embodiments, the X-ray controller 38 may be configured to provide fast-kVp switching of the X-ray source 12 so as to rapidly switch the source 12 to emit X-rays at the respective different polychromatic energy spectra in succession during an image acquisition session.

For example, in a dual-energy imaging context, the X-ray controller 38 may operate the X-ray source 12 so that the X-ray source 12 alternately emits X-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, the fast-kVp switching operation performed by the X-ray controller 38 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

As noted above, the X-ray source 12 may be configured to emit X-rays at one or more energy spectra. Though such emissions may be generally described or discussed as being at a particular energy (e.g., 80 kVp, 140 kVp, and so forth), the respective X-ray emissions at a given energy are actually along a continuum or spectrum and may, therefore, constitute a polychromatic emission centered at, or having a peak strength at, the target energy.

The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer 42 may include or communicate with one or more non-transitory memory devices 46 that can store data processed by the computer 42, data to be processed by the computer 42, or instructions to be executed by a processor 44 of the computer 42. For example, a processor of the computer 42 may execute one or more sets of instructions stored on the memory 46, which may be a memory of the computer 42, a memory of the processor, firmware, or a similar instantiation. In accordance with present embodiments, the memory 46 stores sets of instructions that, when executed by the processor, perform image processing methods as discussed herein (e.g., performance of iMMC).

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Figure 2A:
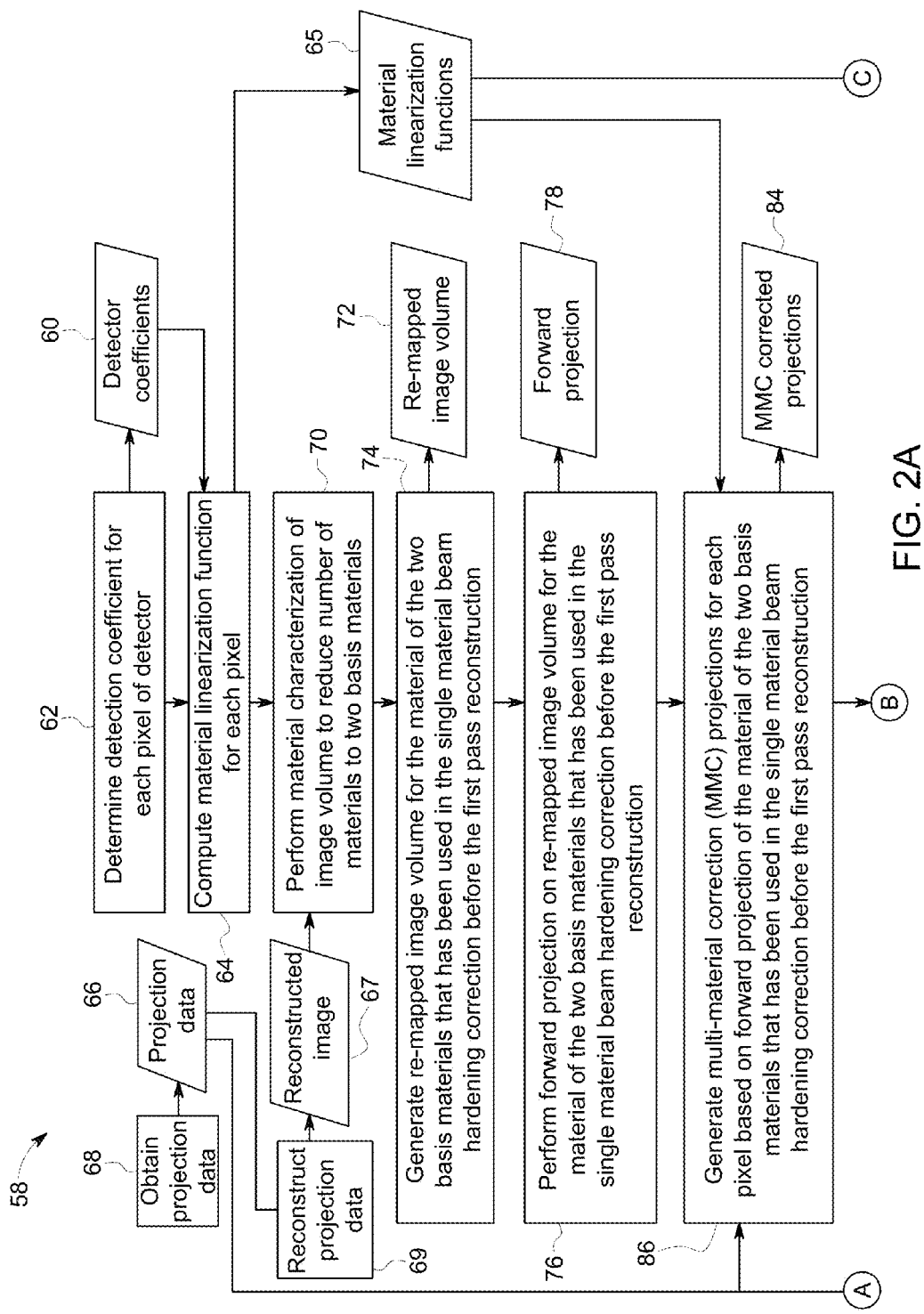
FIGS. 2A and 2B illustrate an embodiment of a method for performing iterative multi-material correction on projection data.
Figure 2B:
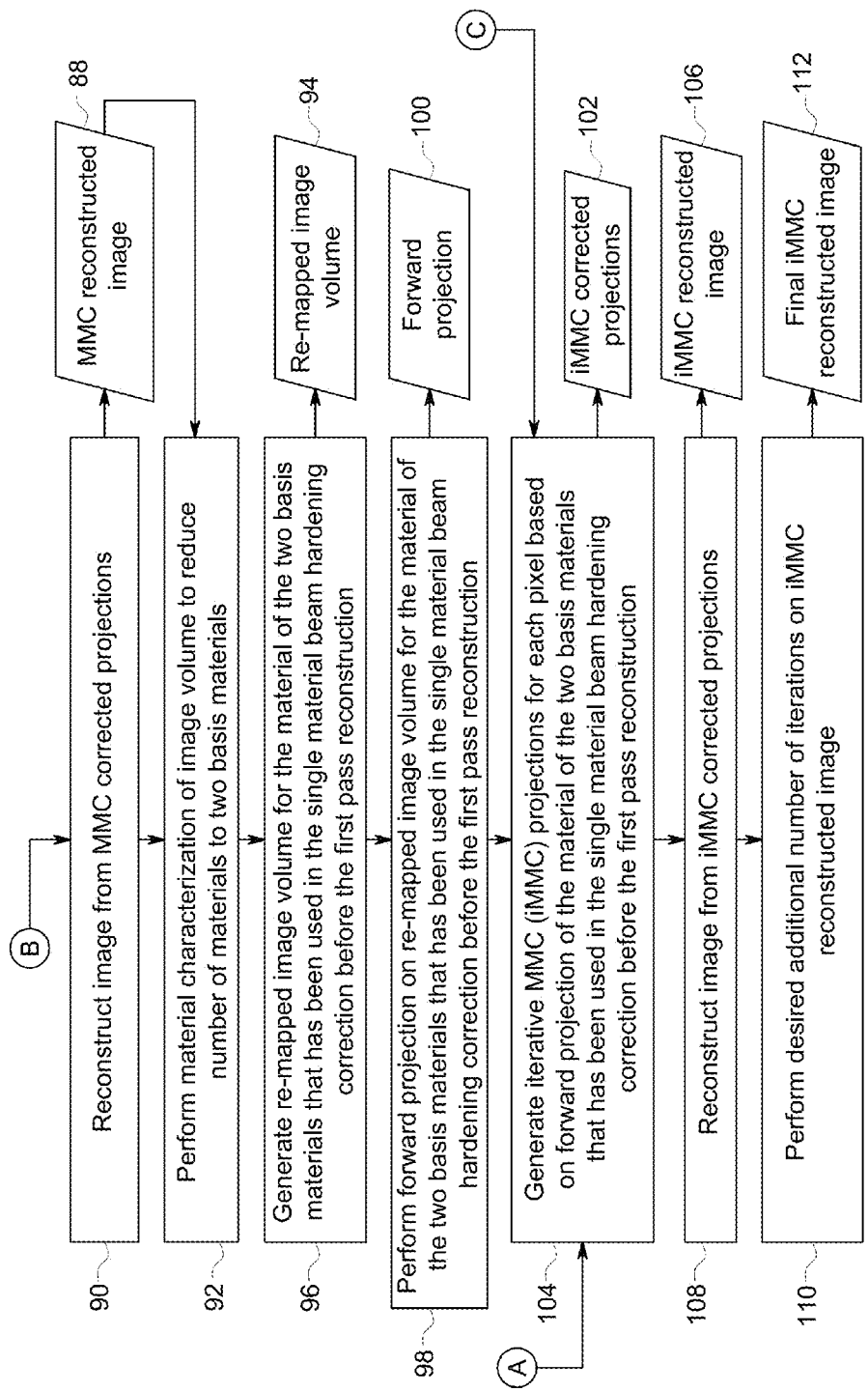

Keeping in mind the operation of the system 10 and, specifically, the X-ray source 12 discussed above with respect to FIG. 1, FIGS. 2A and 2B illustrate a process flow diagram of an embodiment of a method 58 for performing iMMC on projection data (e.g., in the form of datasets). Any suitable application-specific or general-purpose computer having a memory and processor may perform some or all of the steps of the method 58. By way of example, as noted above with respect to FIG. 1, the computer 42 and associated memory 46 may be configured to perform the method 58. For example, the memory 46, which may be any tangible, non-transitory, machine-readable medium (e.g., an optical disc, solid state device, chip, firmware), may store one or more sets of instructions that are executable by a processor of the computer 42 to perform the steps of method 58. In accordance with present embodiments, the processor, in performing method 58, may generate one or more images corrected via multiple rounds of iMMC.

Turning to FIG. 2, in the depicted implementation, the method 58 includes determining detector coefficients 60 for each pixel of the detector 28 (block 62). The detector coefficients 60 are only obtained once for each pixel and may be used for subsequent scans. The detector coefficients 60 are a function of the incident photon energy of each individual pixel. In one embodiment, the detector coefficients 60 are captured from the data of 4 kVp air scans during spectral calibration. The detector coefficients enable the modeling of the detector signals. The detector coefficient 60 of pixel i is expressed in polynomial form in the following equation:

$$\epsilon(E, i) = \Sigma_0^{N-1} X_n(i) E^n, \quad (1)$$

where $\epsilon(E, i)$ represents the detection coefficient, E represents the photon energy, i represents the pixel index, $X_n(i)$ represents detector coefficients expressed in polynomial form, and N represents the number of kVp air scans during the spectral calibration. N is based on the number of kVp stations. For example, N may range from 4 to 5. The detection efficiency factor may depend on a number of factors such as different kVps and different filtrations. In certain embodiments, the $X_n(i)$ values may be stored, e.g., in memory 46, for use in iMMC.

The detector coefficients 60 are utilized in computing a material linearization function (e.g., mapping function) 65 or beam hardening projection error for each pixel (block 64) using projections synthesized through system modeling. The mapping function 65 for each pixel is designed to linearize material projections for the respective pixel. As in MMC, in some embodiments of iMMC, the mapping function 65 is generated based on two basis materials, such as water and iodine. Other basis material pairs may be chosen from other materials such as calcium, metal, and bone. The use of two basis materials enables a complex body composition to be simplified into two components. This reduces the need for forward projections for other materials (i.e., those not selected as the basis materials), while also reducing the complexity of the mapping function.

After determining the mapping function for each pixel, the method 58 includes obtaining projection data 66 (e.g., datasets) (block 68), for example, by acquiring the projection data 66 via the CT system 10 described above. The method 58 also includes reconstructing the projection data 66 from the plurality of pixels into a reconstructed image 67 (e.g., full field of view (FOV) reconstructed image) (block 69). The method 58 includes performing material characterization on an image volume (e.g., voxel) of the reconstructed image (block 70) to reduce a number of materials analyzed in each pixel to two basis materials (e.g., iodine and water). The method 58 further includes generating a remapped image volume 72 (e.g., material-based projection from a re-mapped pixel) (block 74) for water in the case in which the two basis materials are iodine and water, and water BHC has been applied before the first-pass reconstruction. However, in certain embodiments, remapped projections 72 may be obtained for both basis materials (e.g., iodine and water). Further, in certain embodiments, the remapped image volume may be generated for whichever material of the two basis materials has been used in the single material beam hardening correction before the first pass reconstruction.

The method 58 yet further includes performing forward projection on the re-mapped image volume 72 (block 76) to generate a forward projection 78 for at least one basis material (e.g., water) to produce a material-based (e.g., water-based) projection. The method 58 also includes generating MMC corrected projections 84 (e.g., linearized projections) for each pixel based on the material-based projection 78 and initial total projection (e.g., projection data 66) representing attenuation through both of the two basis materials (e.g., iodine and water). In particular, the MMC corrected projections 84 may be based on a summation of the initial total projection and the outcome of the material linearization function 65 or beam hardening projection error (block 86). In certain embodiments, the initial total projection and the outcome of the linearization function 65 or beam hardening projection error may be subtracted from each other. The linearization function 65 is based on the values for the material-based projection 78 and the total initial total projection. In certain embodiments, the initial total projection may be a spectrally corrected total raw projection. The method 58 further includes reconstructing an MMC reconstructed image 88 from the MMC corrected projections 84 (block 90).

In the illustrated embodiment, the method 58 then proceeds through one or more additional rounds of iMMC to further correct the MMC reconstructed image 88. Iterative MMC enables the use of additional rounds by estimating iodine's projection as the line integral of water subtracted from the total projection, as described in more detail below. In the method 58, the MMC reconstructed image 88 is utilized to perform a material characterization of the image volume to once again reduce the number of materials to two basis materials (block 92), and a remapped image volume 94 for water is generated (block 96). Here again, it should be noted that in other embodiments, water may not be the single basis material used in the single material BHC before the first pass reconstruction and, accordingly, the re-mapped image volume may be generated for another type of material. The method 58 then calls for performing forward projection on the re-mapped image volume 94 (block 98) to generate forward projection 100.

The method 58 proceeds by generating iMMC corrected projections 102 for each pixel based on the forward projection of water (block 104). Finally, an iMMC reconstructed image 106 is reconstructed from the iMMC corrected projections (block 108). If desired in the given implementation, any number of additional iterations may be performed on the iMMC reconstructed image 106 (block 110) in order to produce the final desired image 112.

Embodiments of the iMMC method 58 enable the reduction or elimination of multiple errors present when single round MMC is performed, thus avoiding or eliminating the likelihood that over or under corrected images will be generated. For example, iMMC may reduce or eliminate material decomposition and/or re-projection errors. First, with regard to material decomposition errors, the residual beam hardening artifacts on the first-pass reconstructed CT images that are supposed to be corrected by MMC could cause errors in the image-based material decomposition. For example, consider bone (let its CT number be $HU_b$) after material decomposition, with the equivalent iodine fraction estimated by:

$$HU_{io} \approx (HU_{cb} - 1000 m_w \rho_{cb}) \times \frac{HU_b - HU_T}{HU_{cb} - HU_T}, \quad (2)$$

where, $HU_{cb}$ and $\rho_{cb}$ are the CT number and density of cortical bone, respectively, $m_w$ is the decomposition factor for water, and $HU_T$ is the CT number of the material, T. Here, a T-Bone model is used, meaning that a voxel identified as bone will be modeled as a combination of material T and the cortical bone. In practical application, material T is usually air or water.

Assume a phantom with a homogeneous bone (fixed density: $\rho_b$) inside a water cylinder is scanned and perfect material identification has been achieved, then the true CT number of the equivalent iodine should be $$HU_{io} = HU_b - 1000 m_w \rho_b. \quad (3)$$

In contrast, however, the CT number computed with the typically used Air-Bone model using equation (2) is $$HU_{io}^{ABM} = (HU_{cb} - 1000 m_w' \rho_{cb}) \times \frac{HU_b}{HU_{cb}}, \quad (4)$$

where, $m_w'$ is the decomposition factor for water that is actually used in practical implementation. It is seen that the error for the Air-Bone model can be expressed as $$Err_{ABM} = HU_{io}^{ABM} - HU_{io} \quad (5)$$

$$= 1000 \frac{m_w \rho_b HU_{cb} - m_w' \rho_{cb} HU_b}{HU_{cb}}$$

$$= \frac{1000 m_w \rho_{cb}}{HU_{cb}} \left( HU_{b0} - \frac{m_w'}{m_w} HU_b \right)$$

where, $$HU_{b0} = \frac{\rho_b}{\rho_{cb}} HU_{cb},$$

is the expected artifacts free CT number of the bone with density $\rho_b$. Given that strong bone exists, beam hardening of bone would be severe and $HU_b$ might vary dramatically. As a result, it is challenging to find a fixed $m_w'$ that makes the projection of the error image, $Err_{ABM}$, close to zero for various CT scans. In other words, $m_w' = m_w$ would not be a golden solution.

Turning now to re-projection errors, in traditional MMC, the $2^{nd}$-pass beam hardening correction term, $\Delta p$, is computed by a 2D polynomial function, $$\Delta p = \mu_w L_w + \mu_{io} L_{io} - P_t = f_{det}(P_t, P_{io}), \quad (6)$$

where, $P_t$ and $P_{io}$ being the measure total projection after water BHC and the polychromatic projection of iodine, respectively. Theoretically, the polychromatic projection of iodine is defined as $$P_{io} = f_w(p_t) - f_w(p_w), \quad (7)$$

where, $f_w$ denotes the water beam hardening correction function, $p_t$ and $p_w$ are the total projection and the water projection only, whose definitions are $$p_t = -\ln \left( \frac{\int S(E) e^{-(\mu_w(E) L_w + \mu_{io}(E) L_{io})} dE}{\int S(E) dE} \right), \quad (8)$$

and, $$p_w = -\ln \left( \frac{\int S(E) e^{-\mu_w(E) L_w} dE}{\int S(E) dE} \right). \quad (9)$$

From equation 7, it can be seen that the projection of iodine is related to the projection of water.

In practice, $P_{io}$ is estimated by re-projecting the equivalent iodine fraction after material decomposition. This re-projection could have errors. It can be assumed that the reconstructed CT image contains just water and iodine such that material decomposition is not needed. Since water and iodine have quite different ranges of CT number, iodine can be easily separated from water. However, due to the residual beam hardening artifacts, the impacts of iodine usually exceed the regions where the iodine locates. In other words, in most cases the re-projection of identified iodine is not equal to the iodine's projection $P_{io}$ in equation 7.

Due to these potential errors, a single round of MMC may have under or over correction, and the multiple rounds enabled by the presently disclosed iMMC may be advantageous insomuch as less residual beam hardening artifacts exist in the iMMC corrected reconstruction. In the iterative MMC method 58 described above, as compared to single round MMC, re-projection of water instead of iodine is computed and subtracted from the total projection to estimate iodine's polychromatic projection, i.e., $$P_{io}^{rw} = f_w(p_t) - \Sigma \mu_w(i,j,k) L_w(i,j,k), \quad (10)$$

where, the second term represents the line integral of water fraction in the first-pass reconstruction. Iteration is therefore enabled in such an implementation because re-projection of water is always treated as monochromatic.

Indeed, in other embodiments, water's re-projection (approximating $P_w = f_w(p_w)$) may be used directly to compute the second-pass correction-term in the iMMC method with a new 2D polynomial fitting function as $$\Delta p = f_{det}(P_t, P_w). \quad (11)$$

Figure 3A:
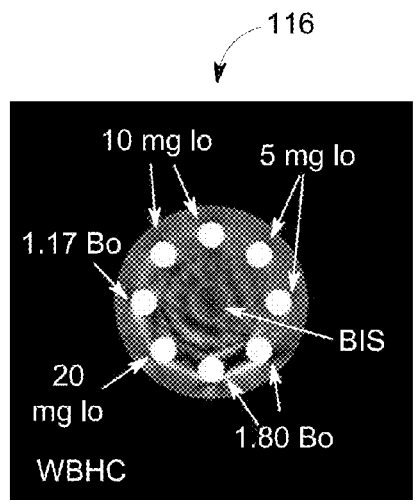
FIG. 3A illustrates an example of an image of a circular water phantom reconstructed using water beam hardening correction.
Figure 3C:
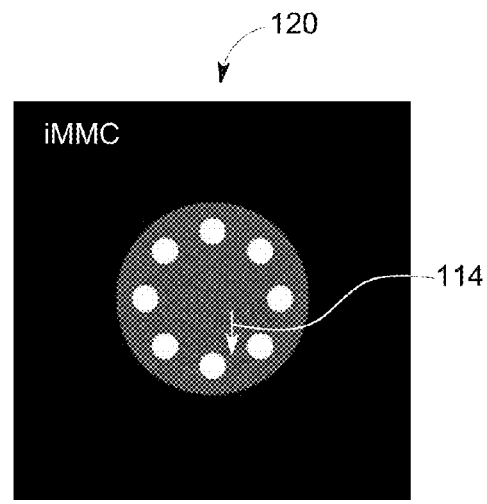
FIG. 3C illustrates an example of an image of a circular water phantom reconstructed using one round of iterative multi-material correction.
Figure 3B:
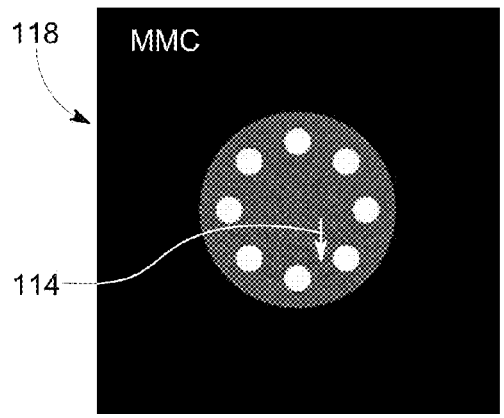
FIG. 3B illustrates an example of an image of a circular water phantom reconstructed using multi-material correction.
Figure 3D:
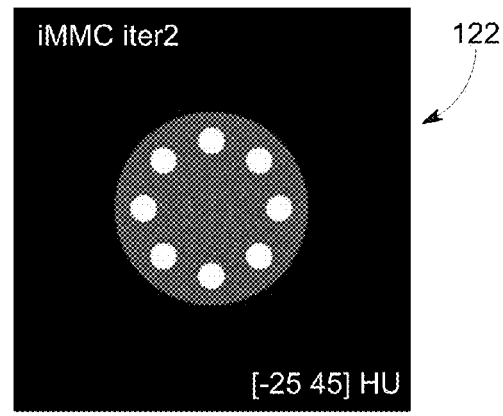
FIG. 3D illustrates an example of an image of a circular water phantom reconstructed using two rounds of iterative multi-material correction.

Various simulation results shown in FIGS. 3A-d, 4A-F, and 5A-D illustrate the effectiveness of the iMMC methods disclosed herein. Particularly, with respect to FIGS. 3A-D, a circular water phantom with various iodine and bone rods and BIS artifacts was simulated. As shown in the simulation 116 of FIG. 3A, a variety of residual beam hardening effects are seen with the BHC reconstruction, but these effects are reduced with MMC, as shown in the simulation 118 of FIG. 3B, and the first round of iMMC, as shown in the simulation 120 of FIG. 3C. While the results of the MMC and the first round of iMMC are predictably similar, a slight over correction, as indicated by arrow 114, is seen after MMC and the first round of iMMC, but this overcorrection is almost eliminated with second round of iMMC, as shown in the simulation 122 of FIG. 3D, thus illustrating the ability of iMMC to address overcorrection that may result from a single round of MMC.

Additionally, an elliptical water phantom with an annulus of high concentration iodine at 50 mg/cc was simulated, and the reconstruction results are shown in FIGS. 4A-F. In particular, the simulated BHC 124 is shown in FIG. 4A, the simulated MMC 126 is shown in FIG. 4B, the simulated first round iMMC is shown in FIG. 4C, the simulated second round iMMC 130 is shown in FIG. 4D, the simulated third round iMMC 132 is shown in FIG. 4E, and the simulated fourth round iMMC 134 is shown in FIG. 4F. Here again, the MMC simulation 126 and the first round iMMC simulation 128 show similar overcorrection in the form of a dark band present near the iodine annulus, as indicated by arrow 136. However, with multiple rounds of iMMC, this overcorrection is reduced, as shown in simulations 130, 132, and 134. That is, in certain embodiments, iMMC not only enables the reduction of artifacts that MMC seeks to address, but also serves as a correction technique for the images produced via single stage MMC.

Figure 5C:
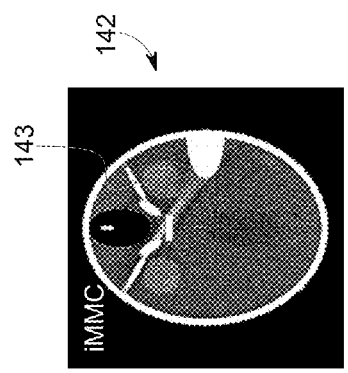
FIG. 5C illustrates an example of an image of a head phantom reconstructed using one round of iterative multi-material correction.
Figure 5D:
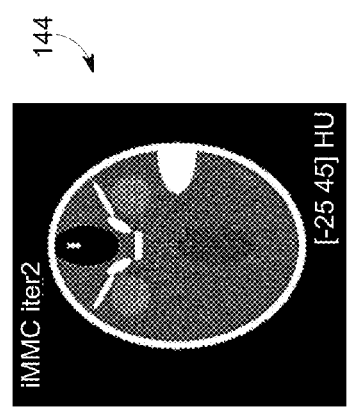
FIG. 5D illustrates an example of an image of a head phantom reconstructed using two rounds of iterative multi-material correction.
Figure 5A:
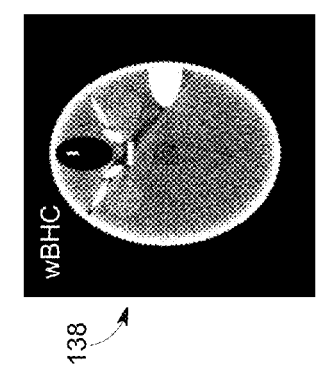
FIG. 5A illustrates an example of an image of a head phantom reconstructed using water beam hardening correction.
Figure 5B:
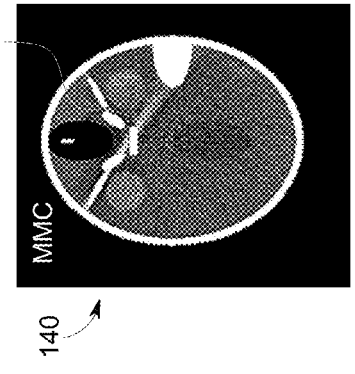
FIG. 5B illustrates an example of an image of a head phantom reconstructed using multi-material correction.

In order to further demonstrate the performance of the iMMC where material decomposition is needed, a head phantom with cortical bone was simulated, and the results are shown in simulations 138, 140, 142, and 144 in FIGS. 5A-D. Here again, the improvements gained by the MMC simulation 140 and the first round iMMC simulation 142 have similar results, and overcorrection is seen in the path of strong bones, as shown by arrows 141 and 143. However, after a second round of iMMC, as shown in FIG. 5D, the overcorrection is almost eliminated without tuning parameters in material decomposition.

Figure 6:
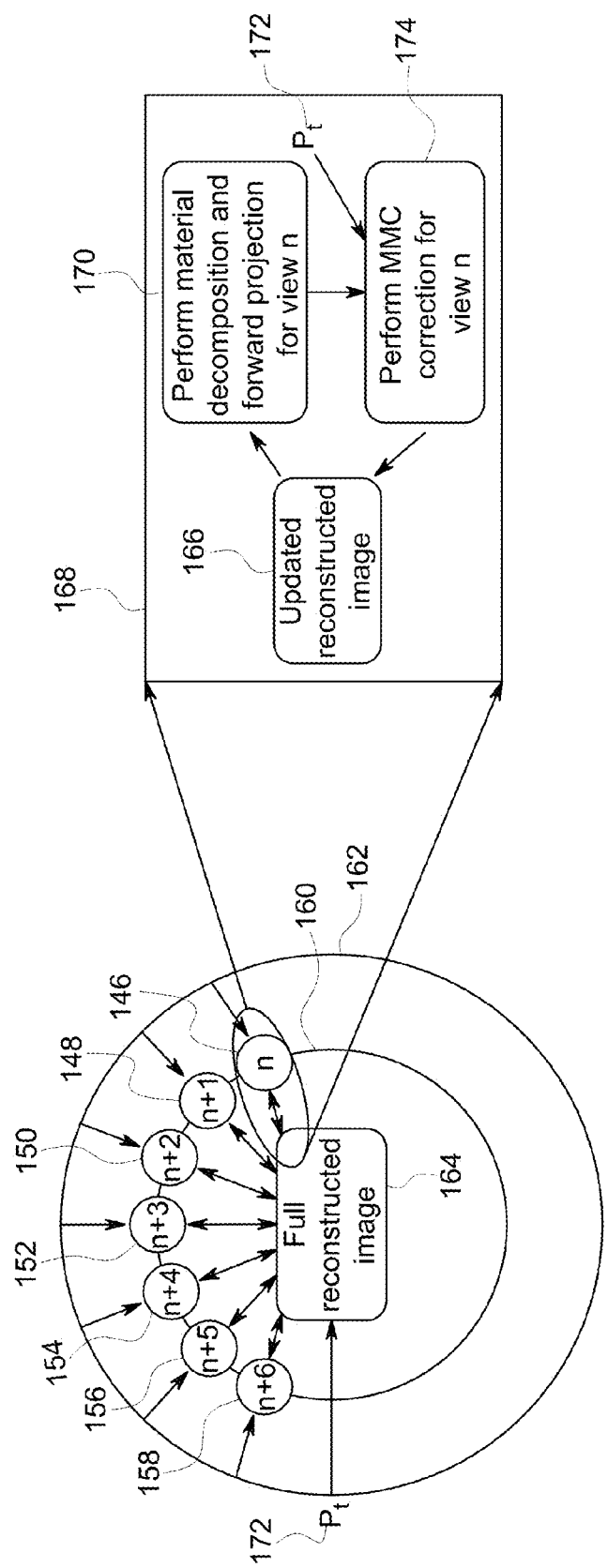
FIG. 6 is a schematic illustrating an embodiment of an incrementally updated image reconstruction method.

Still further, presently disclosed embodiments enable the MMC correction to be quickened by changing the simultaneous update method used in current MMC to a presently disclosed incremental update method illustrated schematically in FIG. 6. Embodiments of the incremental update method may be implemented in such a way that material decomposition and forward projection become more and more accurate as correction moves on from one acquired view to another. As a result, the performance of multi-round iMMC can be achieved in the time of a single round MMC.

Turning now to the schematic in FIG. 6, a plurality of projection views 146, 148, 150, 152, 154, 156, and 158 of an object or subject 160 are successively acquired through operation of imaging gantry 162. It should be noted that six views are shown for illustrative purposes, but any number of projection views may be acquired during implementation. Each of the projection views 146, 148, 150, 152, 154, 156, and 158 contribute to the complete reconstructed image 164. However, the projection views may be successively acquired, for example, such that projection view 146 is acquired first, and projection view 158 is acquired last. In conventional MMC systems, the full final reconstructed image 164 is typically not generated until all the projection views are corrected by the MMC algorithm. However, in the incremental update method, as each iMMC-corrected projection view becomes available, an updated reconstructed image 166 is updated, as shown in block 168. More particularly, as the projection views are corrected (iMMC is performed) and an iMMC-corrected, reconstructed image is generated, updated, and used in subsequent iMMC process (for the next view(s)). For example, as shown in block 168, material decomposition and forward projection is performed for each view (block 170), followed by an MMC correction (block 174) utilizing available projection data 172.

The foregoing incremental update method may offer advantages over the traditional simultaneous update method. For example, the incremental update method may enable the fully reconstructed image 164, which has gone through multiple rounds of iMMC, to be obtained in approximately the same amount of time as would be required for a single round of MMC using the simultaneous update method. Further, because the updated reconstructed image 166 is used in subsequent iMMC process (for the next view(s)), the material decomposition and forward projection become more and more accurate as the correction proceeds from one projection view to the next. Additionally, the iMMC effectively becomes a post-reconstruction processing step, thus rendering the time necessary to perform iMMC less critical to the whole data processing chain.

Further, it should be noted that the order of applying the incremental MMC on the acquired projection views may vary, depending on implementation-specific considerations. For example, in one embodiment, the applied order may be view-by-view such that the incremental MMC is applied in the order in which the views are acquired. In another embodiment, the applied order may be a segment-by-segment update such that incremental MMC is first performed on selected sections of the acquired views and then subsequently on the intermediate sections. In other embodiments, the updating may be random, multi-resolution (e.g., first view, second view, third view, fourth view, sixth view, eight view, tenth view, eleventh view, first view, second view, third view, eleventh view), or any other desired order for applying the incremental MMC on the measured projection views, not limited to those described herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    acquiring projection data of an object from a plurality of pixels, wherein the projection data corresponds to different angular projection views of the object acquired during a scan operation;
    determining a detector coefficient for each pixel of the plurality of pixels;
    computing a material linearization function for each pixel of the plurality of pixels;
    applying a water beam hardening correction to the acquired projection data from the plurality of pixels;
    reconstructing the single material beam hardening corrected projection data from the plurality of pixels into a reconstructed image;
    performing material characterization and decomposition of an image volume of the reconstructed image to reduce a number of materials analyzed in the image volume to only water and iodine;
    generating a re-mapped water image volume;
    performing forward projection on at least the re-mapped water image volume to produce a water-based projection;
    generating multi-material corrected projections for each pixel based on the water-based projection and a total projection attenuated by the scanned object such that the material linearization function is based on the water-based projection and the total projection;
    reconstructing a multi-material corrected image from the multi-material corrected projections; and
    performing one or more iterations of a multi-material correction on the multi-material corrected image to reduce beam hardening artifacts.

2. The method of claim 1, wherein performing one or more iterations of the multi-material correction comprises:
    performing material characterization and decomposition of an image volume of the multi-material corrected image to reduce a number of materials analyzed in the image volume of the multi-material corrected image to water and iodine;
    generating a re-mapped image volume for water;
    performing forward projection on at least the re-mapped image volume for water to produce an iterative water-based projection; and
    generating iterative multi-material corrected projections based on the iterative water-based projection and the total projection attenuated by the scanned object.

3. The method of claim 1, wherein performing one or more iterations of a multi-material correction on the multi-material corrected image comprises estimating a projection value for iodine by subtracting the line integral of equivalent water from the total projection.

4. The method of claim 2, comprising reconstructing an iterative multi-material corrected image from the iterative multi-material corrected projections.

5. A method, comprising:
    acquiring projection data of an object from a plurality of pixels, wherein the projection data corresponds to different angular projection views of the object acquired during a scan operation;
    determining a detector coefficients for each pixel of the plurality of pixels;
    computing a material linearization function for each pixel of the plurality of pixels;
    applying a single material beam hardening correction to the acquired projection data from the plurality of pixels;
    reconstructing the single material beam hardening corrected projection data from the plurality of pixels into a reconstructed image;
    performing material characterization and decomposition of an image volume of the reconstructed image to reduce a number of materials analyzed in the image volume to two basis materials and performing forward projection for the first acquired projection view of the object to produce a single material-based projection;
    performing a multi-material correction for the first acquired projection view of the object to generate a first multi-material corrected projection, such that the material linearization function is based on the single material-based projection and the first multi-material corrected projection;
    updating the reconstructed image based on the first multi-material corrected projection to generate an updated reconstructed image;
    performing, one at a time for each of the plurality of acquired projection views of the object, material characterization and decomposition of an image volume of the updated reconstructed image and forward projection, wherein each projection view corresponds to a different angular orientation between the object and an X-ray source;
    performing a multi-material correction for each of the plurality of acquired projection views of the object one at a time to generate a plurality of multi-material corrected projections; and
    updating the updated reconstructed image based on the plurality of multi-material corrected projections as the plurality of multi-material corrected projections are generated.

6. The method of claim 5, wherein updating the updated reconstructed image comprises updating the updated reconstructed image with each of the plurality of multi-material corrected projections in the order in which the plurality of acquired views were acquired.

7. The method of claim 5, wherein updating the updated reconstructed image comprises updating the updated reconstructed image with each of the plurality of multi-material corrected projections in the order corresponding to predetermined imaged segments.

8. The method of claim 5, wherein updating the updated reconstructed image comprises updating the updated reconstructed image with each of the plurality of multi-material corrected projections randomly without regard to the order in which the plurality of acquired views were acquired.

9. The method of claim 5, wherein the two basis materials comprise iodine and water.

10. A system, comprising:
an imager configured to acquire projection data of an object, wherein the projection data comprises a plurality of projection views; and
a processor configured to determine a detector coefficient for each pixel of a plurality of pixels, compute a material linearization function for each pixel of the plurality of pixels, to generate a multi-material corrected, reconstructed image of the object, to generate a plurality of multi-material corrected projection views by materially decomposing the reconstructed image, forward projecting, and multi-materially correcting each of the plurality of projection views, and to update the multi-material corrected, reconstructed image of the object with each of the plurality of multi-material corrected projection views such that the material linearization function is based on the single material-based projection and the multi-material corrected projection views.

11. The system of claim 10, wherein the processor is configured to generate each of the plurality of multi-material corrected projection views one at a time as each of the plurality of projection views is acquired.

12. The system of claim 10, wherein the processor is configured to generate each of the plurality of multi-material corrected projection views and to update the multi-material corrected, reconstructed image of the object in an order that corresponds to the order in which the plurality of projection views are acquired.

13. The system of claim 10, wherein the processor is configured to generate each of the plurality of multi-material corrected projection views and to update the multi-material corrected, reconstructed image of the object in an order that corresponds to predetermined segments of the imaged object.

14. The system of claim 10, wherein the processor is configured to generate each of the plurality of multi-material corrected projection views and to update the multi-material corrected, reconstructed image of the object in a randomly determined order with respect to the order in which the plurality of projection views are acquired.

15. A system, comprising:
an imager configured to acquire projection data during a scan of an object, wherein the projection data corresponds to different angular views of the object acquired during the scan; and
a reconstructor configured to determine a detector coefficient for each pixel of a plurality of pixels, compute a material linearization function for each pixel of the plurality of pixels, reconstruct the acquired projection data into a reconstructed image, to utilize the reconstructed image to perform a multi-material correction on the acquired projection data using only two basis materials to generate a multi-material corrected reconstructed image, and to utilize the multi-material corrected reconstructed image to perform one or more iterations of the multi-material correction on the projection data to generate an iteratively corrected multi-material corrected image;
wherein the material linearization function is based on a single material-based projection and a total projection attenuated by the object.

16. The system of claim 15, wherein the multi-material correction comprises estimating a projection of iodine by subtracting the line integral of equivalent water from a total projection in the projection data.

17. The system of claim 15, wherein the reconstructor is configured to incrementally update the iteratively corrected multi-material corrected image as the projection data is acquired.

18. The system of claim 17, wherein the reconstructor is configured to incrementally update the iteratively corrected multi-material corrected image in a random order with respect to the order in which each projected view of the acquired projection data is acquired.

19. The system of claim 17, wherein the reconstructor is configured to incrementally update the iteratively corrected multi-material corrected image in a multi-resolution order.

* * * * *